(12) United States Patent
Boppana et al.

(10) Patent No.: US 11,720,228 B2
(45) Date of Patent: Aug. 8, 2023

(54) SYSTEMS AND METHODS FOR TRANSFORMING AN INTERACTIVE GRAPHICAL USER INTERFACE ACCORDING TO MACHINE LEARNING MODELS

(71) Applicant: Evernorth Strategic Development, Inc., St. Louis, MO (US)

(72) Inventors: Adithya Chowdary Boppana, Dublin, OH (US); Christopher R. Markson, Hawthorne, NJ (US); Pritesh J. Shah, Paramus, NJ (US); Jiawei Kuang, St. Louis, MO (US); Keith L. Widmer, Grapevine, TX (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 15 days.

(21) Appl. No.: 17/394,647

(22) Filed: Aug. 5, 2021

(65) Prior Publication Data
US 2023/0049853 A1 Feb. 16, 2023

(51) Int. Cl.
*G06N 20/00* (2019.01)
*G16H 20/10* (2018.01)
*G06F 3/0482* (2013.01)
*G06F 9/451* (2018.01)
*G06F 16/22* (2019.01)

(52) U.S. Cl.
CPC ............ *G06F 3/0482* (2013.01); *G06F 9/451* (2018.02); *G06F 16/22* (2019.01); *G06N 20/00* (2019.01); *G16H 20/10* (2018.01)

(58) Field of Classification Search
CPC ........ G06F 3/0482; G06F 9/451; G06F 16/22; G16H 20/10; G06N 20/00
See application file for complete search history.

(56) References Cited

U.S. PATENT DOCUMENTS

| | | | |
|---|---|---|---|
| 10,339,695 B2 | 7/2019 | Petkov | |
| 10,452,992 B2 | 10/2019 | Lee | |
| 10,453,456 B2 | 10/2019 | Nicholls | |
| 10,573,315 B1 | 2/2020 | Nicholls | |
| 10,592,554 B1 * | 3/2020 | Merritt | G06N 20/20 |
| 10,621,491 B2 | 4/2020 | Vallée | |
| 10,643,138 B2 | 5/2020 | Bellala | |

(Continued)

*Primary Examiner* — Beau D Spratt
(74) *Attorney, Agent, or Firm* — Miller Johnson

(57) ABSTRACT

A computerized method for transforming an interactive graphical user interface according to machine learning includes selecting a persona, loading a data structure associated with the selected persona, and generating the interactive graphical user interface. The method includes, in response to a user selecting a first selectable element, inputting a first set of explanatory variables to a first trained machine learning model to generate a first metric, and transforming the user interface according to the selected persona and the first metric. The method includes, in response to the user selecting a second selectable element, inputting a second set of explanatory variables to a second trained machine learning model to generate a second metric, and transforming the user interface according to the selected persona and the second metric. In various implementations, first metric is a first probability of the persona being approved for a first prior authorization prescription.

20 Claims, 13 Drawing Sheets

(56) References Cited

U.S. PATENT DOCUMENTS

| | | | |
|---|---|---|---|
| 10,855,712 B2 | 12/2020 | Oliner | |
| 10,904,599 B2 | 1/2021 | Sarkhel | |
| 2018/0158010 A1* | 6/2018 | Greenberger | G06Q 10/063112 |
| 2018/0365385 A1* | 12/2018 | Cooney | G16H 20/60 |
| 2019/0392295 A1 | 12/2019 | Oi | |
| 2020/0058041 A1 | 2/2020 | Bharwani | |
| 2020/0152307 A1* | 5/2020 | Ambrose | G16H 20/10 |
| 2020/0279641 A1* | 9/2020 | Nida | G16H 15/00 |
| 2021/0110343 A1* | 4/2021 | Lagneaux | H04L 9/321 |
| 2022/0044818 A1* | 2/2022 | Chang | G16H 50/30 |
| 2022/0272124 A1* | 8/2022 | Zawadzki | H04M 15/62 |
| 2022/0277764 A1* | 9/2022 | Ciliberti | G10L 15/063 |

* cited by examiner

SYSTEMS AND METHODS FOR TRANSFORMING AN INTERACTIVE GRAPHICAL USER INTERFACE ACCORDING TO MACHINE LEARNING MODELS

FIELD

The present disclosure relates to user interface adaptation and, more particularly, to transforming a user interface according to metrics generated by a trained machine learning model.

BACKGROUND

Currently, entities such as high-volume pharmacies offer drug management programs, which may be implemented on local machines or via cloud-based servers. For example, a user who is a member of a pharmacy can employ a user device to create an account via a web portal in order to access the drug management program. Each user may be able to access the same information and may be presented with an identical user interface. Similarly, a support representative or an analyst working for the pharmacy may access information based on data structures generated for one or more users via one or more user interfaces.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computerized method for transforming an interactive graphical user interface according to machine learning is presented. The method includes selecting a persona from a data store, loading, into a data processing module, a data structure associated with the selected persona, and generating the interactive graphical user interface. The interactive graphical user interface may include a first selectable element and a second selectable element. In response to a user selecting the first selectable element, the method may include loading, at the data processing module, a first trained machine learning model, loading, at the data processing module, a first set of explanatory variables from the data structure, inputting, at the data processing module, the first set of explanatory variables to the first trained machine learning model to generate a first metric, and transforming the user interface according to the selected persona and the first metric.

In response to the user selecting the second selectable element, the method may include loading, at the data processing module, a second trained machine learning model, loading, at the data processing module, a second set of explanatory variables from the data structure, inputting, at the data processing module, the second set of explanatory variables to the second trained machine learning model to generate a second metric, and transforming the user interface according to the selected persona and the second metric. The first metric may be a probability of a user associated with the persona being approved for a first prior authorization prescription. In other features, the second metric may be a second probability of the user associated with the persona being approved for a second prior authorization prescription.

In other features, the method may include transforming the user interface according to the selected persona and the first metric by loading, at the data processing module, a first threshold value, and determining whether the first metric is less than the first threshold value. In response to determining that the first metric is less than the first threshold value, the method may include generating an interactive user interface element having a first selectable option and a second selectable option. In response to the user selecting the first selectable option, the method may include sending the data structure associated with the selected persona to a remote user and transforming the user interface to display a negative approval message.

In other features, the method may include transforming the user interface to display the negative approval message in response to the user selecting the second selectable option. In other features, the method may include transforming the user interface to display a positive approval message in response to determining that the first metric is not less than the first threshold value.

In other features, the method may include transforming the user interface according to the selected persona and the second metric by loading, at the data processing module, a second threshold value, and determining whether the second metric is less than the second threshold value. In response to determining the second metric is less than the second threshold value, the method may include generating an interactive user interface element having a first selectable option and a second selectable option. In response to the user selecting the first selectable option, the method may include sending the data structure associated with the selected persona to a remote user and transforming the user interface to display a negative approval message.

In other features, the method may include transforming the user interface to display the negative approval message in response to the user selecting the second selectable option. In other features, the method may include transforming the user interface to display a positive approval message in response to determining that the second metric is not less than the second threshold value.

A computerized method for transforming a user interface according to machine learning is presented. The method may include selecting a persona from a data store, loading, into a data processing module, a data structure associated with the selected persona, and determining, at the data processing module, whether a condition is present in the data structure. In response to determining the condition is not present in the data structure, the method may include loading, at the data processing module, a first trained machine learning model, loading, at the data processing module, a first set of explanatory variables from the data structure, inputting, at the data processing module, the first set of explanatory variables to the first trained machine learning model to generate a first metric, and transforming the user interface according to the selected persona and the first metric.

In response to determining that the condition is present in the data structure, the method may include loading, at the data processing module, a second trained machine learning model, loading, at the data processing module, a second set of explanatory variables from the data structure, inputting, at the data processing module, the second set of explanatory variables to the second trained machine learning model to generate a second metric, and transforming the user interface according to the selected persona and the second metric. The first metric may be a probability of a user associated with the persona being approved for a first prior authorization prescription. In other features, the condition may be a presence of a diagnosis for rheumatoid arthritis. In other features, the second metric may be a second probability of the user associated with the persona being approved for a second prior authorization prescription.

In other features, the method includes transforming the user interface according to the selected persona and the first metric by loading, at the data processing module, a first threshold value, and determining whether the first metric is less than the first threshold value. In response to determining that the first metric is less than the first threshold value, the method may include generating an interactive user interface element having a first selectable option and a second selectable option. In response to the user selecting the first selectable option, the method may include sending the data structure associated with the selected persona to a remote user and transforming the user interface to display a negative approval message.

In other features, the method includes transforming the user interface to display the negative approval message in response to the user selecting the second selectable option. In other features, the method includes transforming the user interface to display a positive approval message in response to determining that the first metric is not less than the first threshold value.

In other features, the method includes transforming the user interface according to the selected persona and the second metric by loading, at the data processing module, a second threshold value and determining whether the second metric is less than the second threshold value. In response to determining that the second metric is less than the second threshold value, the method includes generating an interactive user interface element having a first selectable option and a second selectable option. In response to the user selecting the first selectable option, the method includes sending the data structure associated with the selected persona to a remote user and transforming the user interface to display a negative approval message.

In other features, the method includes transforming the user interface to display the negative approval message in response to the user selecting the second selectable option. In other features, the method includes transforming the user interface to display a positive approval message in response to determining that the second metric is not less than the second threshold value.

A system for transforming a user interface according to machine learning is presented. The system may include a first data store including a persona and a data structure associated with the persona, a second data store including at least one of a first trained machine learning model and a second trained machine learning model and at least one of a first set of explanatory variables and a second set of explanatory variables, and a processor operatively coupled to the first data store and the second data store. The processor may be configured by a set of instructions to generate a graphical user interface including a first selectable element and a second selectable element.

In response to a user selecting the first selectable element, the processor may be configured by the set of instructions to input the first set of explanatory variables to the first trained machine learning model to generate a first metric and transform the user interface according to the persona and the first metric. In response to the user selecting the second selectable element, the processor may be configured by the set of instructions to input the second set of explanatory variables to the second trained machine learning model to generate a second metric and transform the user interface according to the persona and the second metric. The first metric may be a first probability of a user associated with the persona being approved for a first prior authorization prescription. In other features, the second metric may be a second probability of the user associated with the persona being approved for a second prior authorization prescription.

In other features, the second data store may include a threshold value. The processor may be further configured by the set of instructions to determine whether the first metric is less than the threshold value, and generate an interactive user interface element having a first selectable option and a second selectable option in response to determining the first metric is less than the threshold value. In response to the user selecting the first selectable option, the processor may be configured to send the data structure associated with the persona to a remote user and transform the user interface to display a negative approval message.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Introduction

Figure 1:
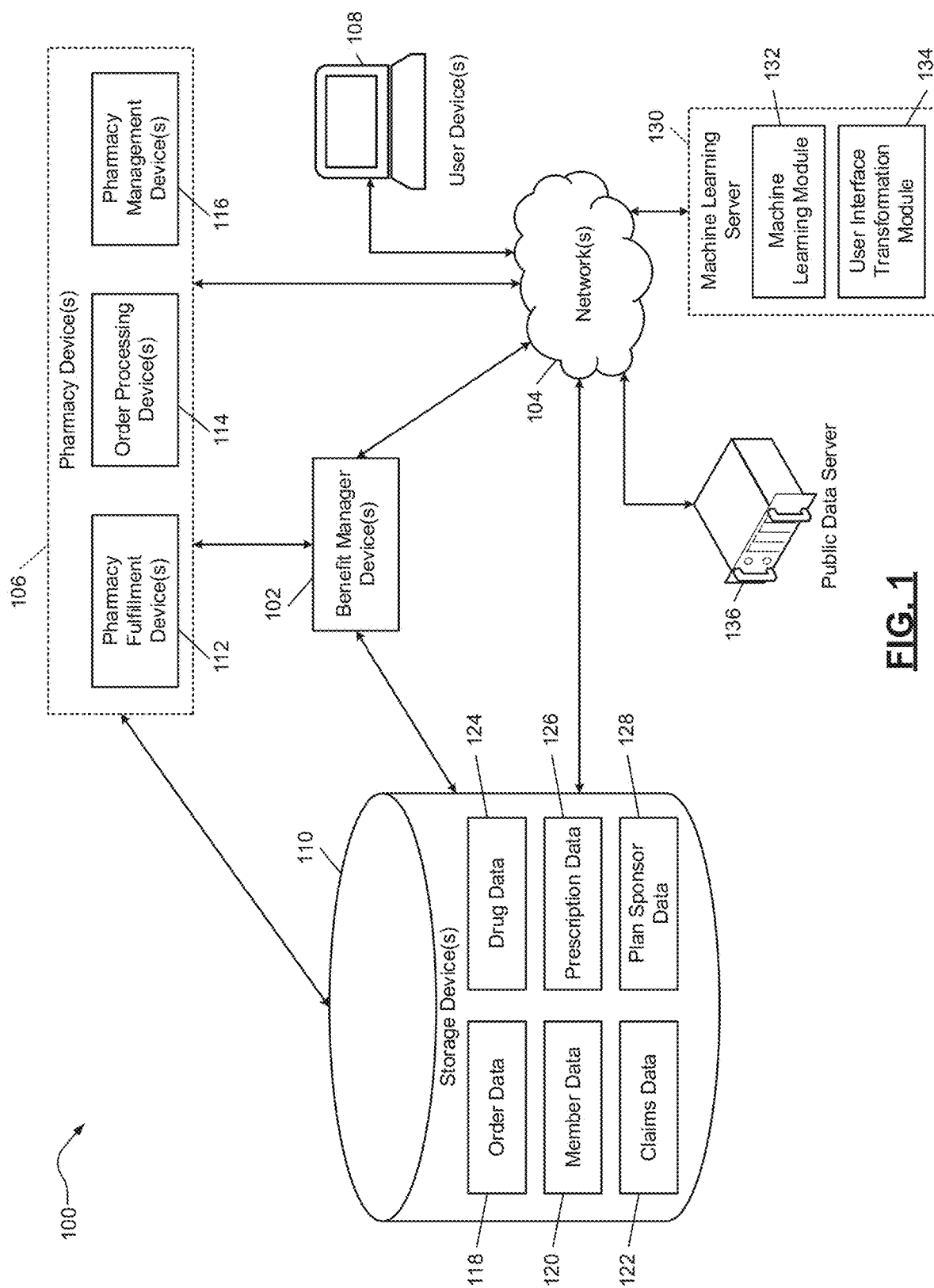
FIG. 1 is a functional block diagram of an example system including a high-volume pharmacy.

Adapting a user interface based on metrics generated by a trained machine learning model provides a personalized user interface in an automated manner directly to a user. In various implementations, user interface adaptations based on the machine-learning-generated metrics can also be provided to support representatives and analysts. The machine-learning-generated metrics may be automatically determined by a bespoke machine learning model built and trained for the specific application.

In various implementations, the machine-learning model may be built and trained using data stored in a storage device of a pharmacy—for example, member data stored in the storage device of the pharmacy. The trained machine learning model may be used to determine one or more metrics by analyzing member data for one or more members.

Adapting a user interface for a support representative or an analyst provides a personalized user interface based on probability scores or data structures, which may be generated from data related to one or more users and/or populations of users stored on a storage device. In various implementations, user interface adaptation based on the probability scores or data structures can also be provided to support representatives and analysts when using their respective devices. The probability scores or data structures may be generated based on data stored in a storage device of a pharmacy—for example, member data stored in the storage device of the pharmacy. Data specific to a user or group of users may be referred to as a persona.

Once determined, the machine-learning-generated metrics may be used to customize the user interface displayed to the user, analyst, and/or support representative. For example, based on the machine-learning generated metrics, a probability that a prior authorization would be approved for a member upon manual review may be automatically calculated, and the user interface may be transformed according to the probability. Prior authorizations are management processes that may be used by insurance companies to determine whether a prescribed medication should be covered under a benefit plan. In various implementations, the user interface may be an interactive graphical user interface that generates one or more interactive elements. Upon a user selecting one of the interactive elements, an appropriate trained machine learning model corresponding to the scenario associated with the interactive element may be loaded, and the user interface may automatically calculate a probability that the prior authorization would be approved.

In various implementations, the user interface may be transformed according to the calculated probability. For example, the system may automatically determine whether or not to approve the prior authorization based on the metrics calculated by the trained machine learning model. In various implementations, if the system automatically determines that the prior authorization should be authorized, the user interface may be transformed accordingly. In various implementations, if the system automatically determines that the prior authorization should not be authorized, the user interface may be transformed accordingly, and member data may be automatically forwarded to a pharmacist, physician, or other appropriate specialist for manual review.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order.

The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, age, date of birth, address (including city, state, and zip code), telephone number, e-mail address, medical history, prescription drug history, etc. In various implementations, the prescription drug history may include a prior authorization claim history—including the total number of prior authorization claims, approved prior authorization claims, and denied prior authorization claims. In various implementations, the prescription drug history may include previously filled claims for the member, including a date of each filled claim, a dosage of each filled claim, the drug type for each filled claim, a prescriber associated with each filled claim, and whether the drug associated with each claim is on a formulary (e.g., a list of covered medication).

In various implementations, the medical history may include whether and/or how well each member adhered to one or more specific therapies. The member data 120 may also include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. In various implementations, the member data 120 may include an eligibility period for each member. For example, the eligibility period may include how long each member is eligible for coverage under the sponsored plan. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member). In various implementations, the claims data 122 may include a percentage of prior authorization cases for each prescriber that have been denied, and a percentage of prior authorization cases for each prescriber that have been approved.

The drug data 124 may include drug name (e.g., technical name and/or common name), other names by which the drug is known, active ingredients, an image of the drug (such as in pill form), etc. The drug data 124 may include information associated with a single medication or multiple medications. For example, the drug data 124 may include a numerical identifier for each drug, such as the U.S. Food and Drug Administration's (FDA) National Drug Code (NDC) for each drug.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
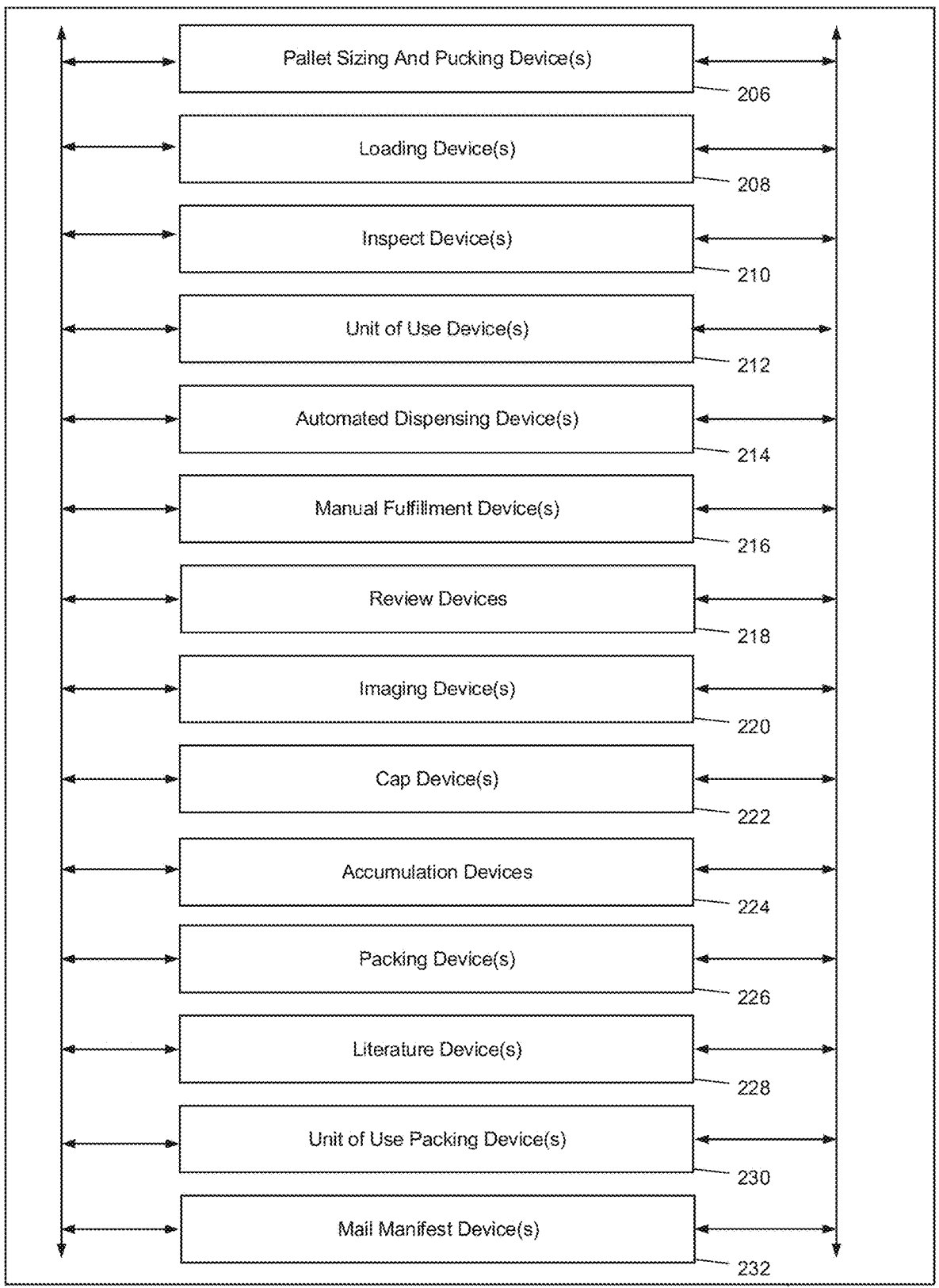
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
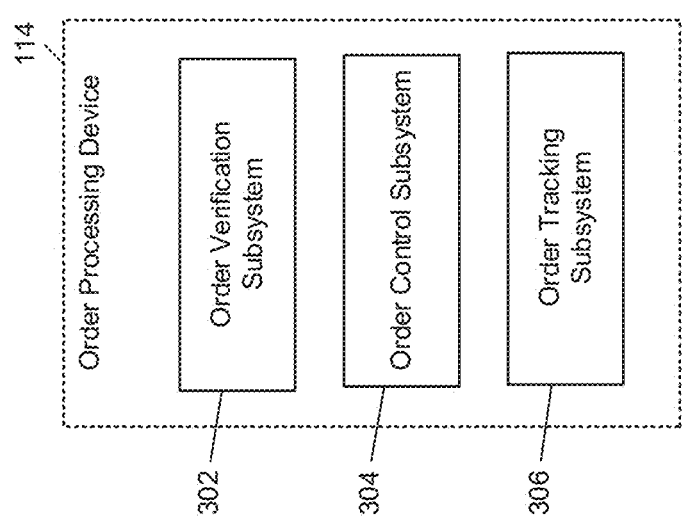
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Machine Learning Server and Other Hardware Components

Referring back to FIG. 1, the system 100 may also include a machine learning server 130. The machine learning server 130 may include one or more software and/or hardware modules, such as a machine learning module 132 and a user interface transformation module 134. In various implementations, the machine learning module 132 and/or the user interface transformation module 134 may be stored on non-transitory computer-readable storage media and accessible by a processor. In various implementations, the machine learning module 132 may include one or more software and/or hardware modules for building a machine learning model, building a training data structure, training the machine learning model using the training data structure, and applying the trained machine learning module in order to generate results. In various implementations, the user interface transformation module 134 may generate and transform a user interface based on the trained machine learning model. For example, the user interface transformation module 134 may generate and transform the user interface based on results generated by the machine learning module 132 applying the trained machine learning model.

In various implementations, the user interface may be generated by a web portal. In various implementations, the machine learning module 132 may be in communication with other components of the system 100 directly or through a network, such as network 104. In various implementations, the system 100 may include one or more data servers, such as public data server 136. In various implementations, the public data server 136 may communicate with other components of the system 100 directly or through a network, such as network 104. In various implementations, the public data server 136 may include demographic data, such as U.S. Census data. In various implementations, the U.S. Census data may include an average individual and/or household income for each geographical subdivision within the United States. In various implementations, each geographical subdivision may be a state, county, city, or a zip code.

Figure 4:
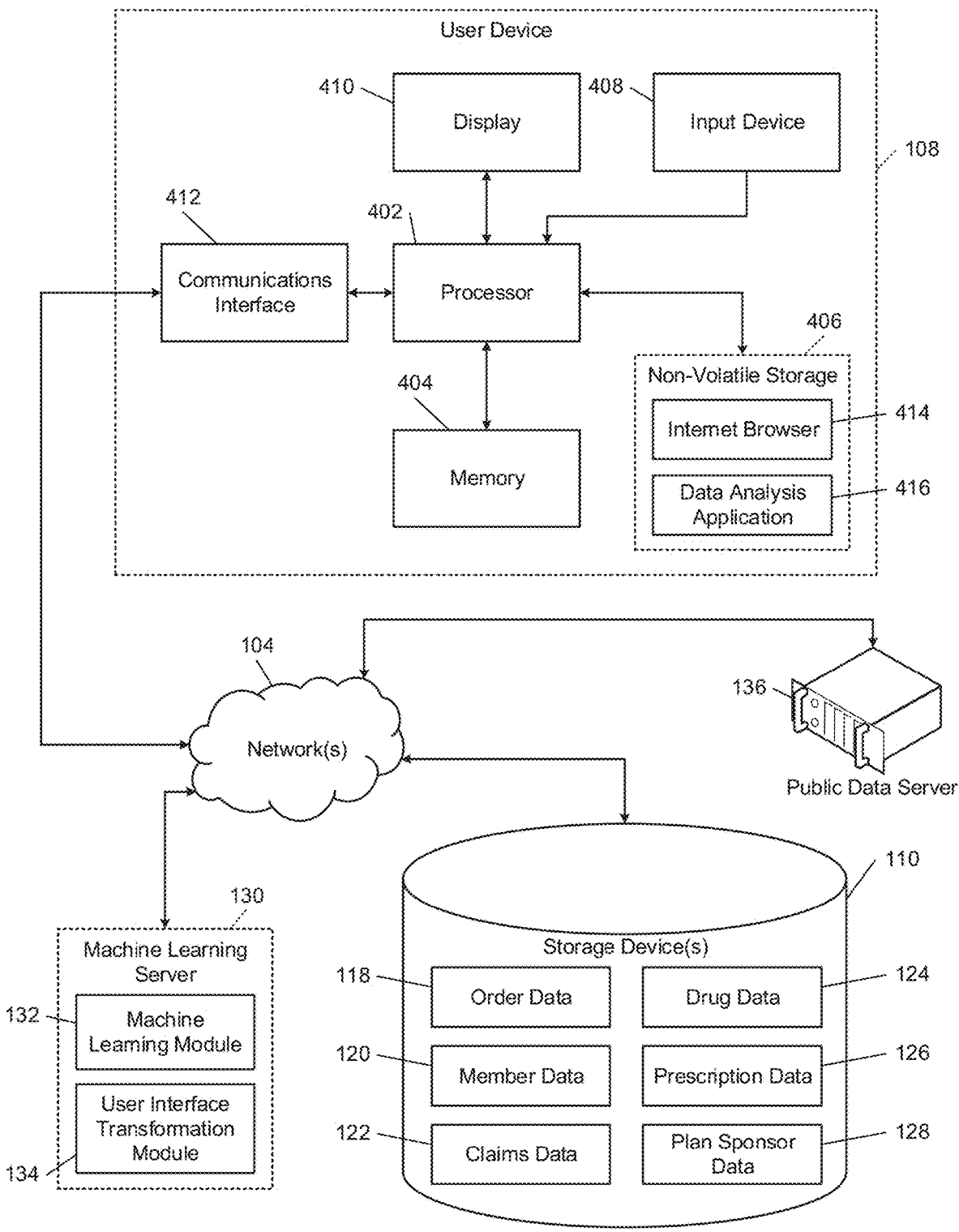
FIG. 4 is a functional block diagram of an example user device.

FIG. 4 is a functional block diagram of an example user device 108. The user device 108 may include a computer or a microprocessor. For example, the user device 108 may include a processor 402, volatile or non-volatile computer memory 404, such as random-access memory (RAM), and computer-readable storage media, such as non-volatile storage 406. In various implementations, the non-volatile storage 406 may include a hard disk drive (HDD), flash memory, and/or any other suitable non-volatile memory or non-volatile storage medium accessible by the processor 402.

The user device 108 may also include one or more input devices, such as input device 408, and one or more output devices, such as display 410. In various implementations, the display 410 may be a touchscreen, and may also serve as an input device. In various implementations, the user device 108 may also include a transceiver, such as communications interface 412. In various implementations, the memory 404, the non-volatile storage 406, the input device 408, display 410, and/or the communications interface 412 may be operatively coupled to the processor 402 and/or each other.

As illustrated in the example of FIG. 4, the processor 402 may communicate with the network 104 through communications interface 412. In various implementations, the processor 402 may access the storage device 110, machine learning server 130, and/or the public data server 136 through the communications interface 412 and the network 104, or directly via the communications interface 412. In various implementations, the non-volatile storage 406 may include one or more hardware and/or software modules for accessing the Internet, such as Internet browser 414, and/or one or more hardware and/or software modules for performing data analysis, such as data analysis application 416.

In various implementations, the Internet browser 414 and/or the data analysis application 416 may access the machine learning module 132 and/or the user interface transformation module 134 via the communications interface 412, the network 104, and/or the web portal generated by the user interface transformation module 134 at the machine learning server 130. In various implementations, the machine learning module 132 and/or the user interface transformation module 134 may access the order data 118, member data 120, claims data 122, drug data 124, prescription data 126, and/or the plan sponsor data 128 on the storage device 110, and/or data stored on the public data server 136.

Flowcharts

Figure 5:
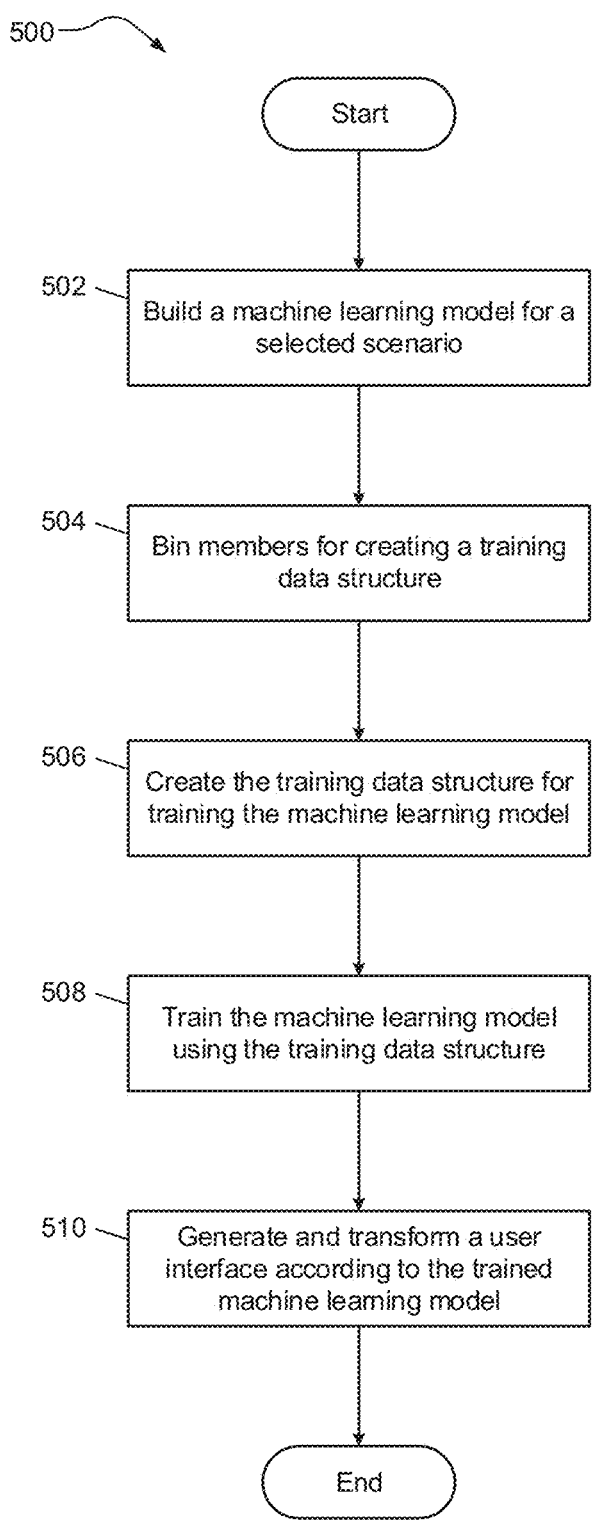
FIG. 5 is a flowchart of an example process according to the principles of the present disclosure.

FIG. 5 is a flowchart of an example process 500 for building and training a machine learning model and transforming an interactive graphical user interface using the trained machine learning model. The process 500 may be performed by the machine learning module 132 and/or the user interface transformation module 134 of the machine learning server 130 of FIGS. 1 and 4. Control, such as a processor at the machine learning server 130, may begin in response to a request received from the Internet browser 414 and/or the data analysis application 416 of the user device 108. In various implementations, control may begin in response to one or more scenarios. In a first scenario, control receives a request to predict a likelihood of one or more members receiving prior authorization for a prescription of a drug. In various implementations, the prescription may include the prescriber's information, the patient or member's information, the recipe (including the medication, the dosage, and the form of the dose), instructions for the member, dispensing instructions, the number of refills, and the prescriber's signature. As one specific example, the drug may be an immunosuppressive drug for treating arthritis or rheumatoid arthritis, such as adalimumab. In various implementations, under the first scenario, the one or more members may not have received a diagnosis for rheumatoid arthritis.

In a second scenario, control receives a request to predict a likelihood of one or more members receiving prior authorization for a prescription of a drug such as adalimumab. In various implementations, under the second scenario, the one or more members may have received an accompanying diagnosis for rheumatoid arthritis. Once the request is received, control begins at 502, where control builds a machine learning module for the selected scenario. For example, if control receives a request under the first scenario, a machine learning model appropriate to the first scenario may be built. In various implementations, if control receives a request under the second scenario, a machine learning model appropriate to the second scenario may be built. After the machine learning model is built, control proceeds to 504.

At 504, control bins members for creating one or more training data structures. For example, control may access member data 120 to identify members (and their associated data) that may be suitable for training the machine learning model. Control proceeds to 506. At 506, control accesses the machine learning module 132 to create the training data structure for training the machine learning model built at 502. For example, the training data structure may be built using data associated with the members binned at step 504. Control proceeds to 508. At 508, control accesses the machine learning module 132 to train the machine learning model using the training data structure generated at 506. Control proceeds to 510. At 510, control accesses the machine learning module 132 and the user interface transformation module 134 to generate and transform a user interface according to the trained machine learning model.

Figure 6:
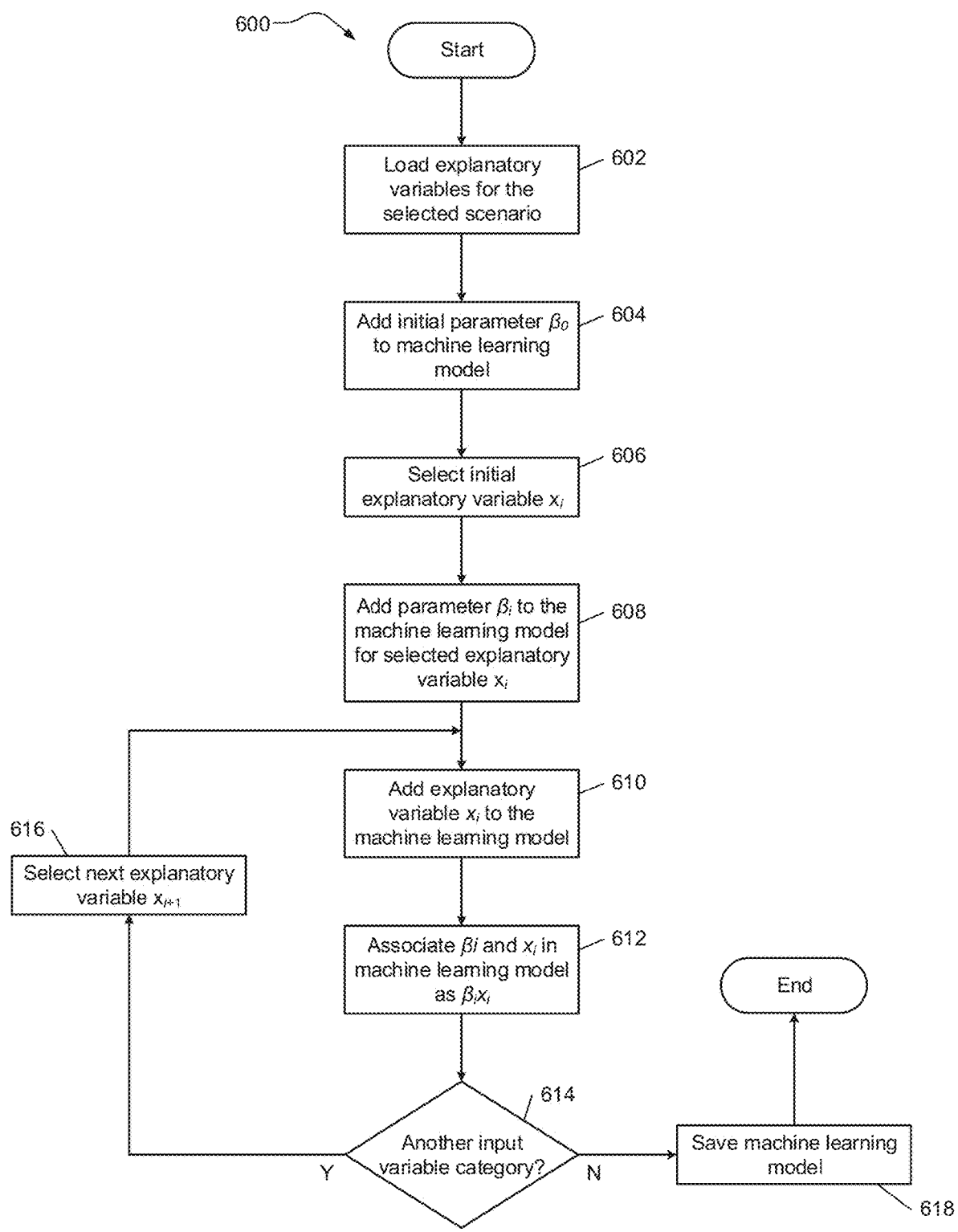
FIG. 6 is a flowchart of an example process for building a machine learning model.

FIG. 6 is a flowchart of an example process 600, which may be performed by the machine learning module 132 of FIGS. 1 and 4, to build a machine learning model at step 502 of process 500 of FIG. 5. At 602, control loads input variables appropriate to the selected scenario. In various implementations, if the selected scenario is the first scenario, control may load some or all of the explanatory variables from Table 1 below as the input variables:

TABLE 1

| i | Description | Explanatory Variable |
|---|---|---|
| 1 | National Drug Code (NDC) number of the prescribed drug (e.g., the prescribed adalimumab) | $x_1$ |
| 2 | Total number of prior authorization cases present for the member in the member data 120 for the last 365 days | $x_2$ |
| 3 | The Most Common Indication description that is associated with the most claims present in the member data 120 | $x_3$ |
| 4 | Numerical rating of the member's adherence to teriparatide therapy retrieved from member data 120 | $x_4$ |
| 5 | Member's state of residence from the member data 120 | $x_5$ |
| 6 | The number of days between the request received at step 602 and the most recent claim present in the member data 120 | $x_6$ |
| 7 | Number of days remaining in the eligibility period for the member from the member data 120 | $x_7$ |
| 8 | Percentage of prior authorization cases for the current prescriber that have been denied within the last 180 days from the claims data 122 | $x_8$ |
| 9 | Percentage of prior authorization cases for the current prescriber that have been approved within the last 180 days from the claims data 122 | $x_9$ |
| 10 | Age of the member from the member data 120 | $x_{10}$ |
| 11 | Number of adjusted claims related to gastrointestinal issues for the member present in the member data 120 | $x_{11}$ |
| 12 | Number of adjusted claims for vitamins, hematinics, and electrolytes for the member present in the member data 120 | $x_{12}$ |
| 13 | Change in dosage for the current claim compared to the previous claim present in member data 120 | $x_{13}$ |

In various implementations, if the selected scenario is the second scenario, control may load some or all of the explanatory variables from Table 2 below as the input variables:

TABLE 2

| i | Description | Explanatory Variable |
|---|---|---|
| 1 | Number of adjusted claims for rheumatology drugs present in the member data 120 for the member | $x_1$ |
| 2 | Number of days the member has been associated with the prescriber in the member data 120 | $x_2$ |
| 3 | Total cost of the claim | $x_3$ |
| 4 | Numerical rating of the member's adherence to teriparatide therapy based on member data 120 | $x_4$ |
| 5 | Number of adjusted retail maintenance non-formulary claims for the member present in member data 120 | $x_5$ |
| 6 | Average income at the member zip code from U.S. Census data present on the public data server 136 | $x_6$ |
| 7 | National Drug Code (NDC) number of the prescribed drug (e.g., the prescribed adalimumab) | $x_7$ |
| 8 | Number of adjusted claims for antiviral drugs present in the member data 120 for the member | $x_8$ |
| 9 | Number of adjusted claims for hormone replacement therapy present in the number data 120 for the member | $x_9$ |

After the appropriate explanatory variables have been loaded for the selected scenario, control proceeds to 604. At 604, control access the machine learning module 132 and adds an initial parameter $\beta_0$ to the machine learning model. In various implementations, the machine learning model may be a logistic regression model, and the initial parameter $\beta_0$ may be the parameter not associated with any explanatory variables. After the initial parameter has been added to the model, control proceeds to 606. At 606, control accesses the machine learning module 132 and selects the initial explanatory variable $x_i$ from the loaded input variable categories. Control then proceeds to 608.

At 608, control accesses the machine learning module 132 to add an i-th parameter $\beta_i$ to the machine learning model. Control then proceeds to 610, where control accesses the machine learning module 132, adds the selected explanatory variable $x_i$ to the machine learning model, and continues to 612. At 612, control accesses the machine learning module 132 and associates $\beta_i$ and $x_i$ in the machine learning model as $\beta_i x_i$. Control switches to 614, where control accesses the machine learning module 132 to determine whether there is another explanatory variable remaining to be added to the machine learning model. If the answer at 614 is yes, control proceeds to 616, selects the next explanatory variable $x_{i+1}$, and proceeds to 610. If at 614 the answer is no, control proceeds to 618 and saves the built machine learning model. Control then ends.

In various implementations, if the selected scenario is the first scenario, then the saved machine learning model may be described according to Equation (1) below, where p represents the predicted probability of the prior authorizing prescription being approved, and where $x_i$ corresponds to the appropriate input variable from Table 1.

$$\log\left(\frac{p}{1-p}\right) = \beta_0 + \beta_1 x_1 + \beta_2 x_2 + \beta_3 x_3 + \beta_4 x_4 + \beta_5 x_5 + \beta_6 x_6 + \beta_7 x_7 + \beta_8 x_8 + \beta_9 x_9 + \beta_{10} x_{10} + \beta_{11} x_{11} + \beta_{12} x_{12} + \beta_{13} x_{13} \quad (1)$$

In various implementations, if the selected scenario is the second scenario, then the saved machine learning model may be described according to Equation (2) below, where p represents predicted probability of the prior authorization prescription being approved, and where $x_i$ corresponds to the appropriate input variable from Table 2.

$$\log\left(\frac{p}{1-p}\right) = \beta_0 + \beta_1 x_1 + \beta_2 x_2 + \beta_3 x_3 + \beta_4 x_4 + \beta_5 x_5 + \beta_6 x_6 + \beta_7 x_7 + \beta_8 x_8 + \beta_9 x_9 \quad (2)$$

In various implementations, the logarithmic functions of Equation (1) and/or Equation (2) may be a natural logarithm.

Figure 7:
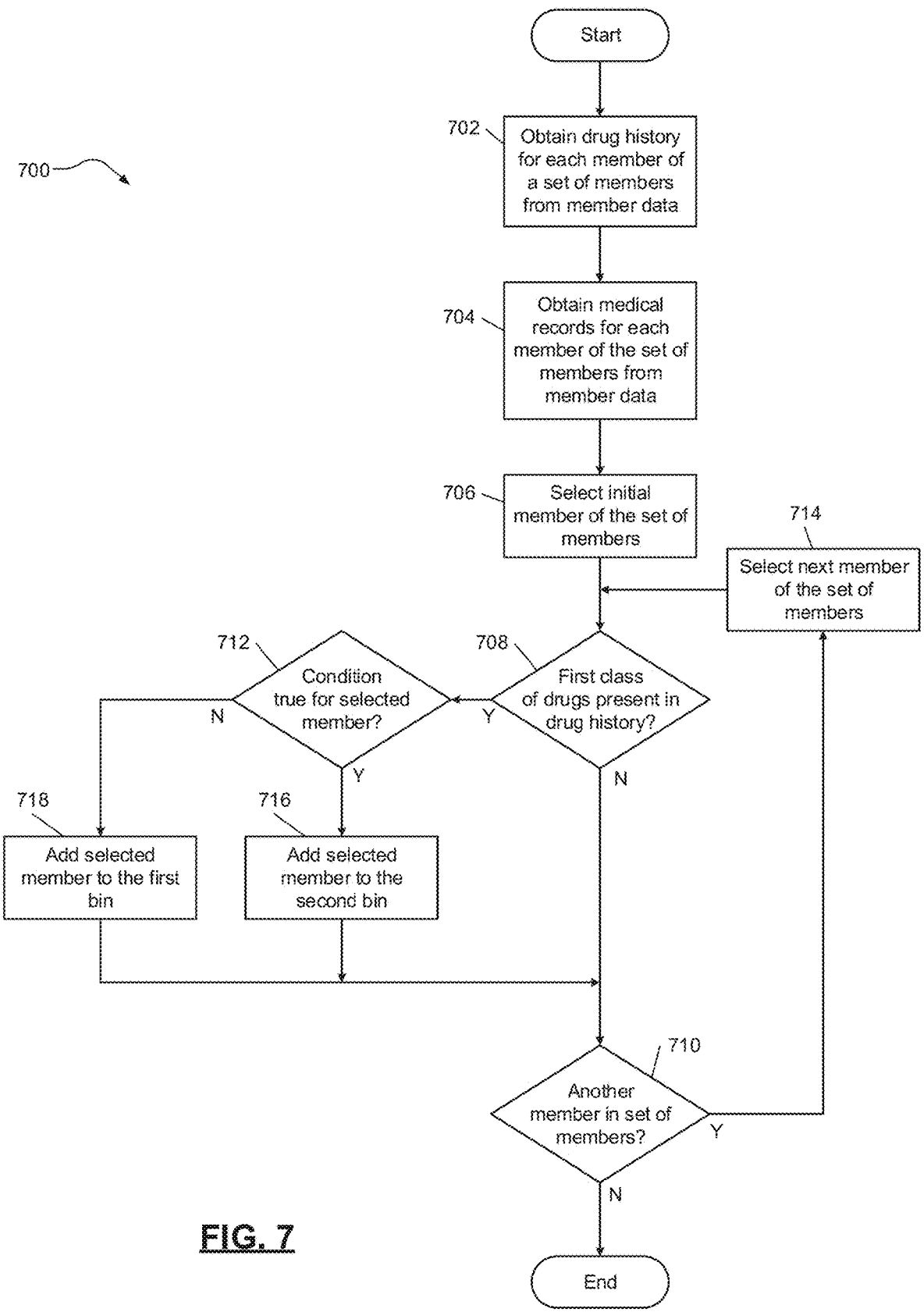
FIG. 7 is a flowchart of an example process for binning members.

FIG. 7 is a flowchart of an example process 700 for binning members at step 504 of process 500 of FIG. 5 for creating the training data structure. Control begins at 702. At 702, control obtains the drug history for each member of a set of members from member data 120. Control proceeds to 704. At 704, control obtains medical records for each member of the set of members from member data 120. Control proceeds to 706. At 706, control selects the initial member of the set of members. Control proceeds to 708. At 708, control determines whether a first class of drugs is present in the drug history of the selected member. In various example, the first class of drugs may be any drug including adalimumab. If at 708, control determines that the first class of drugs is not present in the selected member's drug history, control proceeds to 710. Otherwise, control proceeds to 712. At 710, control determines whether another member is present in the set of members. If at 710, control determines that the answer is yes, control proceeds to select another member of the set of members at 714, and proceeds back to 708.

At 712, control determines whether a condition is true for the selected member. In various implementations, the condition may be whether a positive diagnosis for rheumatoid arthritis is present in the medical records of the selected member. If at 712, the condition is true, control proceeds to 716. If at 712, the condition is false, control proceeds to 718. At 718, control adds the member to a first bin. Control proceeds to 710. At 716, control adds the member to a second bin. Control proceeds to 710. In various implementations, the first bin may contain members whose data will be used to train the machine learning model for the first scenario. In various implementations, the second bin may contain members whose data will be used to train the machine learning model for the second scenario.

Figure 8:
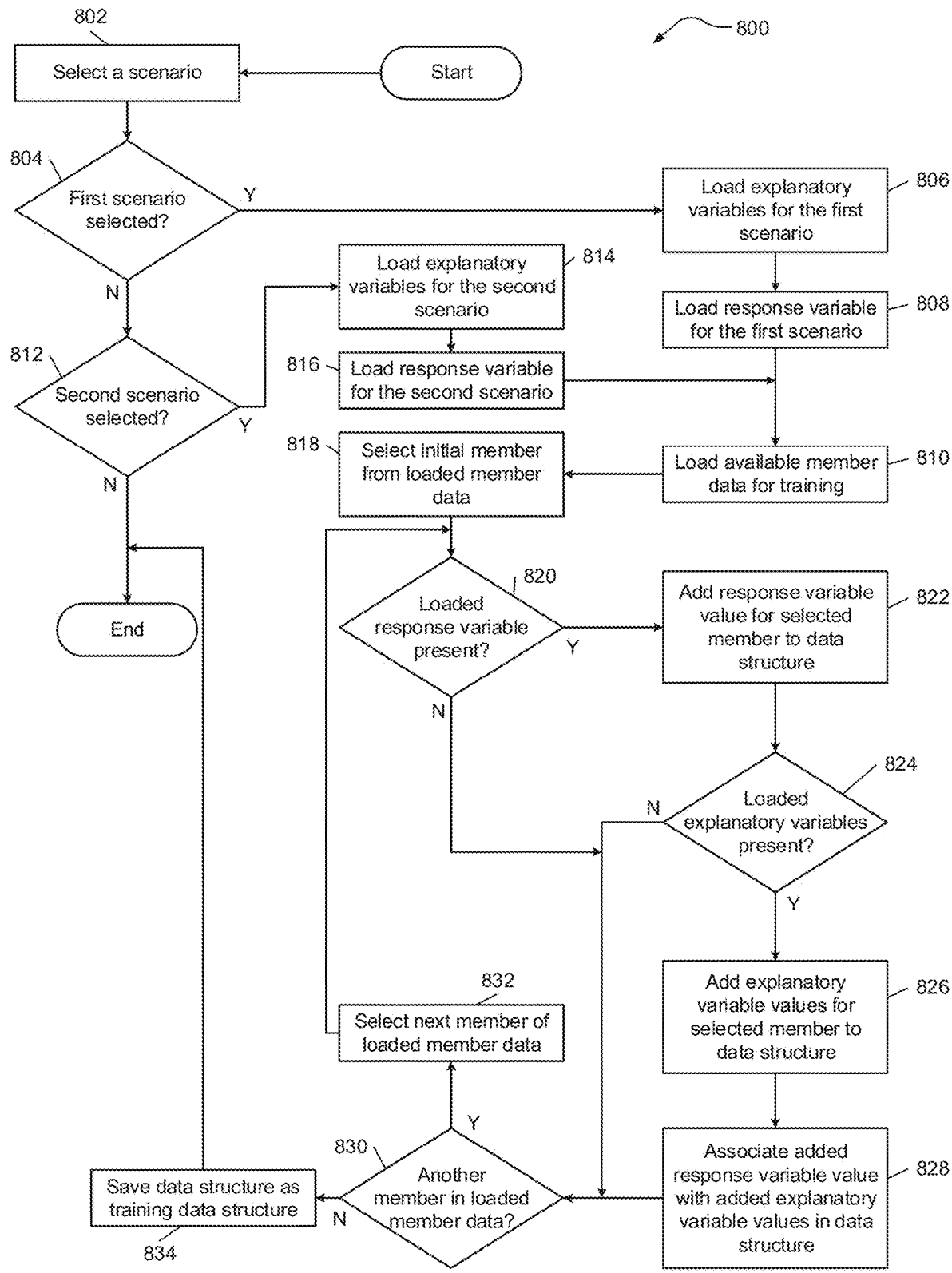
FIG. 8 is a flowchart of an example process for creating a training data structure.

FIG. 8 is a flowchart of an example process 800 for creating the training data structure at step 506 of process 500 of FIG. 5. The training data structure may be used for training the machine learning model built at step 502. Process 800 may be performed by the machine learning module 132 of FIGS. 1 and 4. At 802, control may select a scenario. In various implementations, control may select the first scenario or the second scenario. After the appropriate scenario is selected, control proceeds to 804.

At 804, control determines whether the first scenario was selected. If the first scenario was selected, control proceeds to load explanatory variables for the first scenario at 806. In various implementations, the explanatory variables for the first scenario may include some or all of the explanatory variables previously described at Table 1. Control then proceeds to 808. At 808, control loads a response variable for the first scenario. In various implementations, the response variable for the first scenario may be whether or not a prior authorization claim for adalimumab was approved after manual review. For example, if the prior authorization claim was approved, the response variable might have a value of "1." Otherwise, if the prior authorization claim was not approved, the response variable might have a value of "0." In various implementations, the response variable may be loaded from member data 120. Control continues to 810.

If at 804, control determines that the first scenario was not selected, control proceeds to 812, where control determines whether the second scenario was selected. If at 812, control determines that the second scenario was selected, control proceeds to 814; otherwise, control ends. If after 812, control determines neither the first scenario nor the second scenario was selected, control may prompt the user to select a scenario or generate an error message. At 814, control loads the explanatory variables for the second scenario. In various implementations, the explanatory variables for the second scenario include one or more of the explanatory variables previously described at Table 2. Control then proceeds to 816. At 816, control loads a response variable for the second scenario. In various implementations, the response variable of 816 may be similar to the response variable of 808. Control then proceeds to 810.

At 810, control loads available data from member data 120 for training. For example, if the first scenario was selected, control loads data from member data 120 for the first bin of members. If the second scenario was selected, control loads data from member data 120 for the second bin of members. Control proceeds to 818. At 818, control selects an initial member from the loaded member data, and proceeds to 820.

At 820, control determines whether the loaded response variable is present in the member data for the selected member. If the member data for the selected member contains the loaded response variable, control proceeds to 822. Otherwise, control proceeds to 830. At 822, control adds the response variable value for the selected member to a data structure and proceeds to 824. At 824, control determines whether the loaded explanatory variables are present in the member data for the selected member. If the loaded explanatory variables are present in the member data for the selected member, control proceeds to 826. Otherwise, control proceeds to 830.

At 826, control adds the explanatory variable values for the selected member to the data structure and proceeds to 828. At 828, control associates the added response variable value with the added explanatory variable values in the data structure. Control proceeds to 830. At 830, control determines whether another member who was not previously selected is present in the member data. If control determines another member is present, control proceeds to 832 and selects the next member from the loaded member data. Control then proceeds to 820. If, at 830, control determines that no unselected members are present in the loaded member data, control proceeds to 834, where control saves the data structure as a training data structure. Control then ends.

An example of the saved data structure is shown below in Table 3:

TABLE 3

| Explanatory Variable Value | Response Variable Value |
| --- | --- |
| $x_{1, MEMBER\ 1}$ | 0 or 1 |
| $x_{2, MEMBER\ 1}$ | 0 or 1 |
| $x_{3, MEMBER\ 1}$ | 0 or 1 |
| $x_{4, MEMBER\ 1}$ | 0 or 1 |
| $x_{5, MEMBER\ 1}$ | 0 or 1 |
| $x_{6, MEMBER\ 1}$ | 0 or 1 |
| $x_{7, MEMBER\ 1}$ | 0 or 1 |
| $x_{8, MEMBER\ 1}$ | 0 or 1 |
| $x_{9, MEMBER\ 1}$ | 0 or 1 |

TABLE 3-continued

| Explanatory Variable Value | Response Variable Value |
| --- | --- |
| $x_{10, MEMBER\ 1}$ | 0 or 1 |
| $x_{11, MEMBER\ 1}$ | 0 or 1 |
| $x_{12, MEMBER\ 1}$ | 0 or 1 |
| $x_{13, MEMBER\ 1}$ | 0 or 1 |
| ... | ... |
| $x_{1, MEMBER\ n}$ | 0 or 1 |
| $x_{2, MEMBER\ n}$ | 0 or 1 |
| $x_{3, MEMBER\ n}$ | 0 or 1 |
| $x_{4, MEMBER\ n}$ | 0 or 1 |
| $x_{5, MEMBER\ n}$ | 0 or 1 |
| $x_{6, MEMBER\ n}$ | 0 or 1 |
| $x_{7, MEMBER\ n}$ | 0 or 1 |
| $x_{8, MEMBER\ n}$ | 0 or 1 |
| $x_{9, MEMBER\ n}$ | 0 or 1 |
| $x_{10, MEMBER\ n}$ | 0 or 1 |
| $x_{11, MEMBER\ n}$ | 0 or 1 |
| $x_{12, MEMBER\ n}$ | 0 or 1 |
| $x_{13, MEMBER\ n}$ | 0 or 1 |

Table 3 represents a training data structure built where the first scenario was selected, and there are a total of n members within the available member data for training. For each member, the relevant explanatory variable from Table 1 is loaded and added to the training data structure as numerical explanatory variable value $x_i$, and each explanatory variable value $x_i$ is associated with a numerical response variable value 0 or 1. In various implementations, the response variable indicates whether or not the prior authorization claim for adalimumab for member n was approved upon manual review. An analogous example of a saved data structure for the second scenario is shown below in Table 4:

TABLE 4

| Explanatory Variable Value | Response Variable Value |
| --- | --- |
| $x_{1, MEMBER\ 1}$ | 0 or 1 |
| $x_{2, MEMBER\ 1}$ | 0 or 1 |
| $x_{3, MEMBER\ 1}$ | 0 or 1 |
| $x_{4, MEMBER\ 1}$ | 0 or 1 |
| $x_{5, MEMBER\ 1}$ | 0 or 1 |
| $x_{6, MEMBER\ 1}$ | 0 or 1 |
| $x_{7, MEMBER\ 1}$ | 0 or 1 |
| $x_{8, MEMBER\ 1}$ | 0 or 1 |
| $x_{9, MEMBER\ 1}$ | 0 or 1 |
| ... | ... |
| $x_{1, MEMBER\ n}$ | 0 or 1 |
| $x_{2, MEMBER\ n}$ | 0 or 1 |
| $x_{3, MEMBER\ n}$ | 0 or 1 |
| $x_{4, MEMBER\ n}$ | 0 or 1 |
| $x_{5, MEMBER\ n}$ | 0 or 1 |
| $x_{6, MEMBER\ n}$ | 0 or 1 |
| $x_{7, MEMBER\ n}$ | 0 or 1 |
| $x_{8, MEMBER\ n}$ | 0 or 1 |
| $x_{9, MEMBER\ n}$ | 0 or 1 |

Table 4 represents a training data structure built where the second scenario was selected, and there are a total of n members within the available member data for training. For each member, the relevant explanatory variable from Table 2 is loaded and added to the training data structure as a numerical explanatory variable value $x_i$, and each explanatory variable value $x_i$ is associated with a numerical response variable value 0 or 1. In various implementations, the response variable indicates whether or not the prior authorization claim for adalimumab for member n was approved upon manual review.

Figure 9:
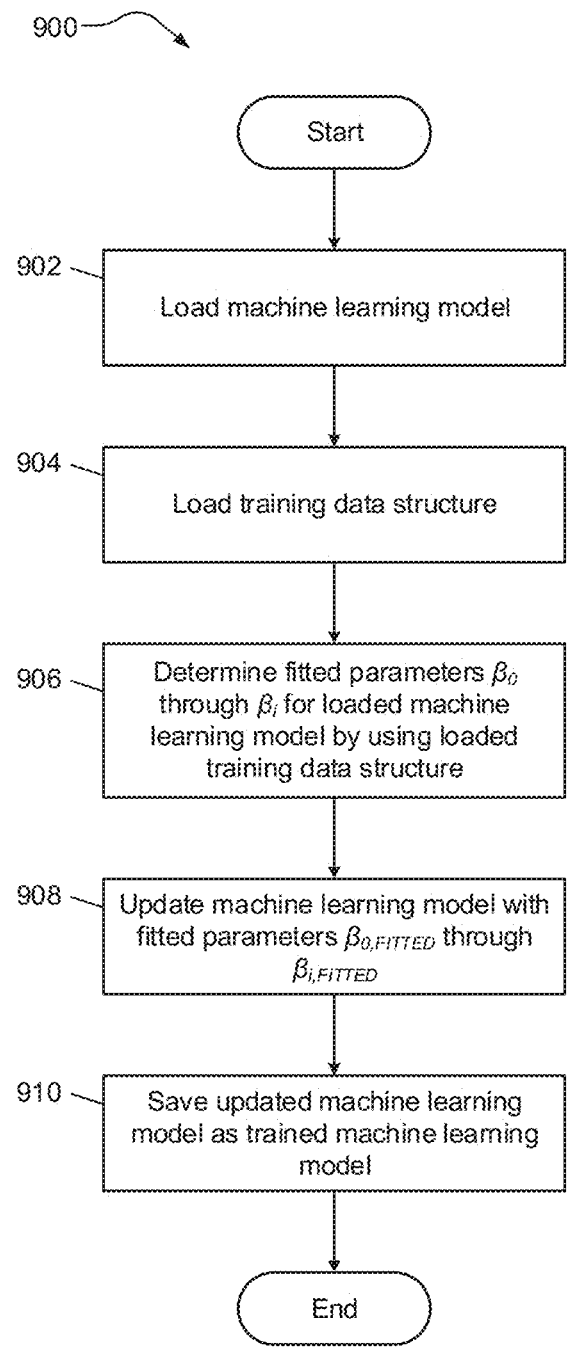
FIG. 9 is a flowchart of an example process for training a machine learning model.

FIG. 9 is a flowchart of an example process 900, which may be performed by the machine learning module 132 of FIG. 4, for training the machine learning model at step 508 of process 500 of FIG. 5. At step 902, control may load the machine learning model saved at step 618 of process 600. In various implementations, if the first scenario is selected, the machine learning model defined by Equation (1) may be loaded. In various implementations, if the second scenario is selected, the machine learning model defined by Equation (2) may be loaded. Control proceeds to 904. At 904, control may load the training data structure saved at step 834 of process 800. For example, if the first scenario is selected, the training data structure of Table 3 may be loaded, or if the second scenario is selected, the training data structure of Table 4 may be loaded. After the training data structure is loaded, control proceeds to 906.

At 906, control determines best fits for each of the parameters $\beta_0$ through $\beta_i$ of the machine learning model of Equation (1) or Equation (2). In various implementations, the training data structure may be represented on a scatter plot. The numerical explanatory variable values may be plotted on the independent axis, while the response variable values may be plotted on the dependent axis. According to the machine learning models of Equations (1) and (2), the logit or log-odds function log $$\left(\frac{p}{1-p}\right)$$

of the output probability p is modeled as a linear function of explanatory variables $x_i$ through $x_j$. Thus, a fitted sigmoid function, such as a fitted logistic function may be used to model the predicted output p. In various implementations, an algorithm such as a maximum-likelihood estimation algorithm may be used to fit the parameters $\beta_0$ through $\beta_i$ of the sigmoid function to the training data structure. In various implementations, the gradient descent algorithm, Broyden-Fletcher-Goldfarb-Shanno (BFGS) algorithm, limited-memory BFGS algorithm, or conjugate gradient algorithm may be used. At 908, if under the first scenario, the machine learning model of Equation (1) may be updated to Equation (3) below, where $\beta_{i,FITTED}$ represents a fitted parameter:

$$\log\left(\frac{p}{1-p}\right) = \quad (3)$$
$$\beta_{0,FITTED} + \beta_{1,FITTED}x_1 + \beta_{2,FITTED}x_2 + \beta_{3,FITTED}x_3 + \beta_{4,FITTED}x_4 +$$
$$\beta_{5,FITTED}x_5 + \beta_{6,FITTED}x_6 + \beta_{1,FITTED}x_7 + \beta_{1,FITTED}x_8 + \beta_{1,FITTED}x_9 +$$
$$\beta_{1,FITTED}x_{10} + \beta_{1,FITTED}x_{11} + \beta_{1,FITTED}x_{12} + \beta_{1,FITTED}x_{13}$$

Similarly, if under the second scenario, the machine learning model of Equation (2) may be updated to Equation (4) below:

$$\log\left(\frac{p}{1-p}\right) = \quad (4)$$
$$\beta_{0,FITTED} + \beta_{1,FITTED}x_1 + \beta_{2,FITTED}x_2 + \beta_{3,FITTED}x_3 + \beta_{4,FITTED}x_4 +$$
$$\beta_{5,FITTED}x_5 + \beta_{6,FITTED}x_6 + \beta_{1,FITTED}x_7 + \beta_{1,FITTED}x_8 + \beta_{1,FITTED}x_9$$

The updated machine learning model of Equation (3) or Equation (4) may be saved as a trained machine learning model at 910.

Figure 10:
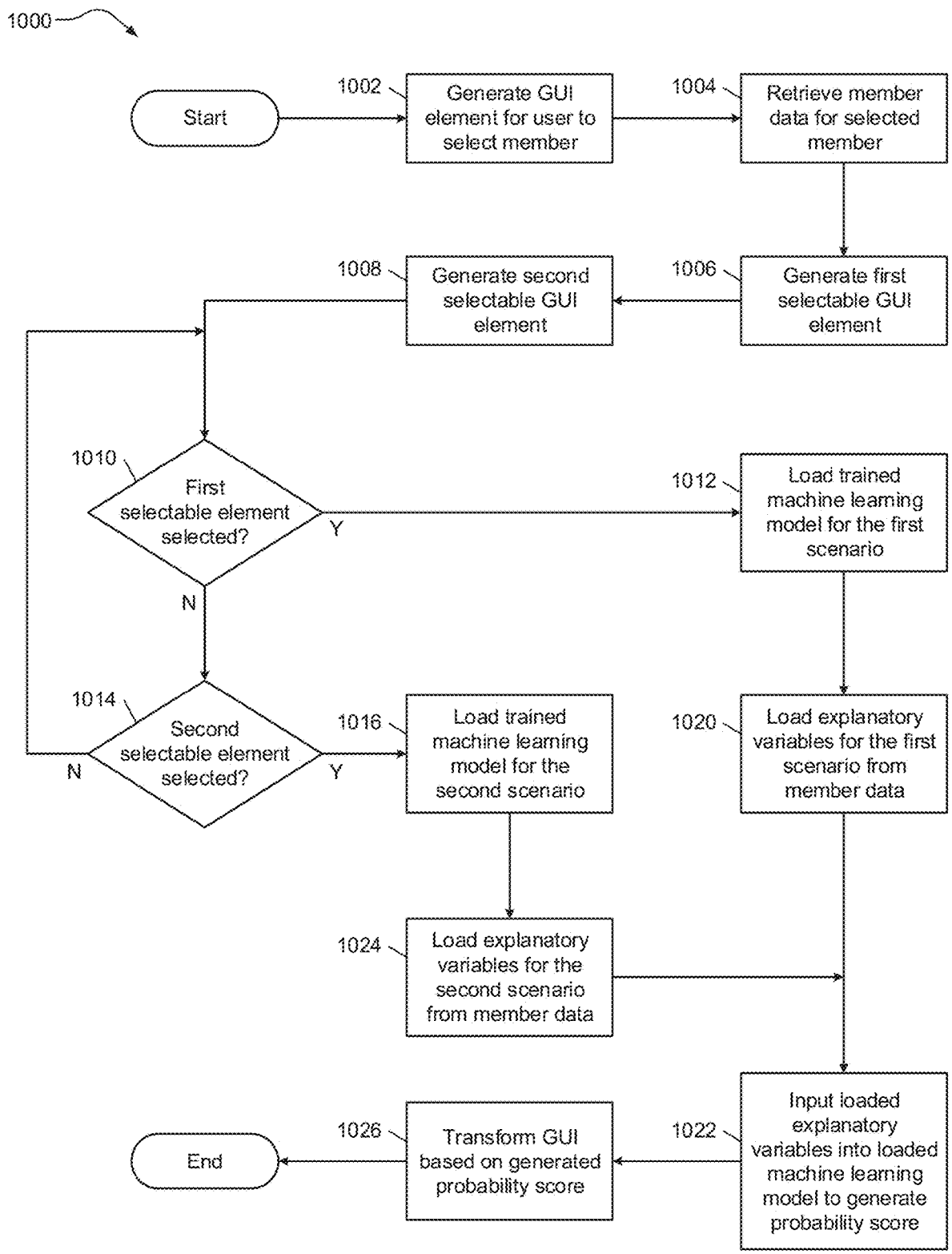
FIG. 10 is a flowchart of an example process for transforming a user interface according to an output of a trained machine learning model.

FIG. 10 is a flowchart of an example process 1000 which may be performed by the machine learning module 132 and/or the user interface transformation module 134 of FIGS. 1 and 4 to generate and transform the user interface according to the trained machine learning model at step 510 of process 500 of FIG. 5. Control begins at 1002 by generating a graphical user interface element for the user to select a member. In various implementations, the graphical user interface element may be a textual search box allowing the user to search for members present in member data 120. In various implementations, the graphical user interface element may be a drop-down menu allowing the user to select a member present in member data 120. After the user selects a member, control proceeds to 1004. At 1004, control retrieves member data for the selected member and proceeds to 1006.

At 1006, control generates a first selectable graphical user interface element. In various implementations, the first selectable graphical user interface element may correspond to the first scenario. In various implementations, the first selectable graphical user interface element may include text and/or graphics describing the first scenario. Control proceeds to 1008. At 1008, control generates a second selectable graphical user interface element. In various implementations, the second selectable graphical user interface element may correspond to the second scenario. In various implementations, the second selectable graphical user interface element may include text and/or graphics describing the second scenario. Control proceeds to 1010.

At 1010, control determines whether the first selectable graphical user interface element has been selected by the user. If at 1010, control determines that the first selectable graphical user interface element has been selected, control proceeds to 1012. Otherwise, control proceeds to 1014. At 1014, control determines whether the second selectable element has been selected by the user. If so, control proceeds to 1016; otherwise, control proceeds returns to 1010.

At 1012, control loads the trained machine learning model for the first scenario. For example, control may load the trained machine learning model described by Equation (3). Control proceeds to 1020. At 1020, control loads the relevant explanatory variables $x_i$ through $x_j$ for the loaded trained machine learning model from the member data 120 for the selected member, and provides the explanatory variables to the trained machine learning model. For example, the explanatory variables may be those defined by Table 1 above. Control proceeds to 1022.

At 1016, control loads the trained machine learning model for the second scenario. For example, control may load the trained machine learning model described by Equation (4). Control proceeds to 1024. At 1024, control loads the relevant explanatory variables $x_i$ through $x_j$ for the loaded trained machine learning model from the member data 120 for the selected member, and provides the explanatory variables to the trained machine learning model. For example, the explanatory variables may be those defined by Table 2 above. Control proceeds to 1022.

At 1022, control inputs the loaded explanatory variables into the loaded machine learning model to generate a probability score p. Control proceeds to 1026 and transforms the graphical user interface based on the generated probability score p.

Figure 11:
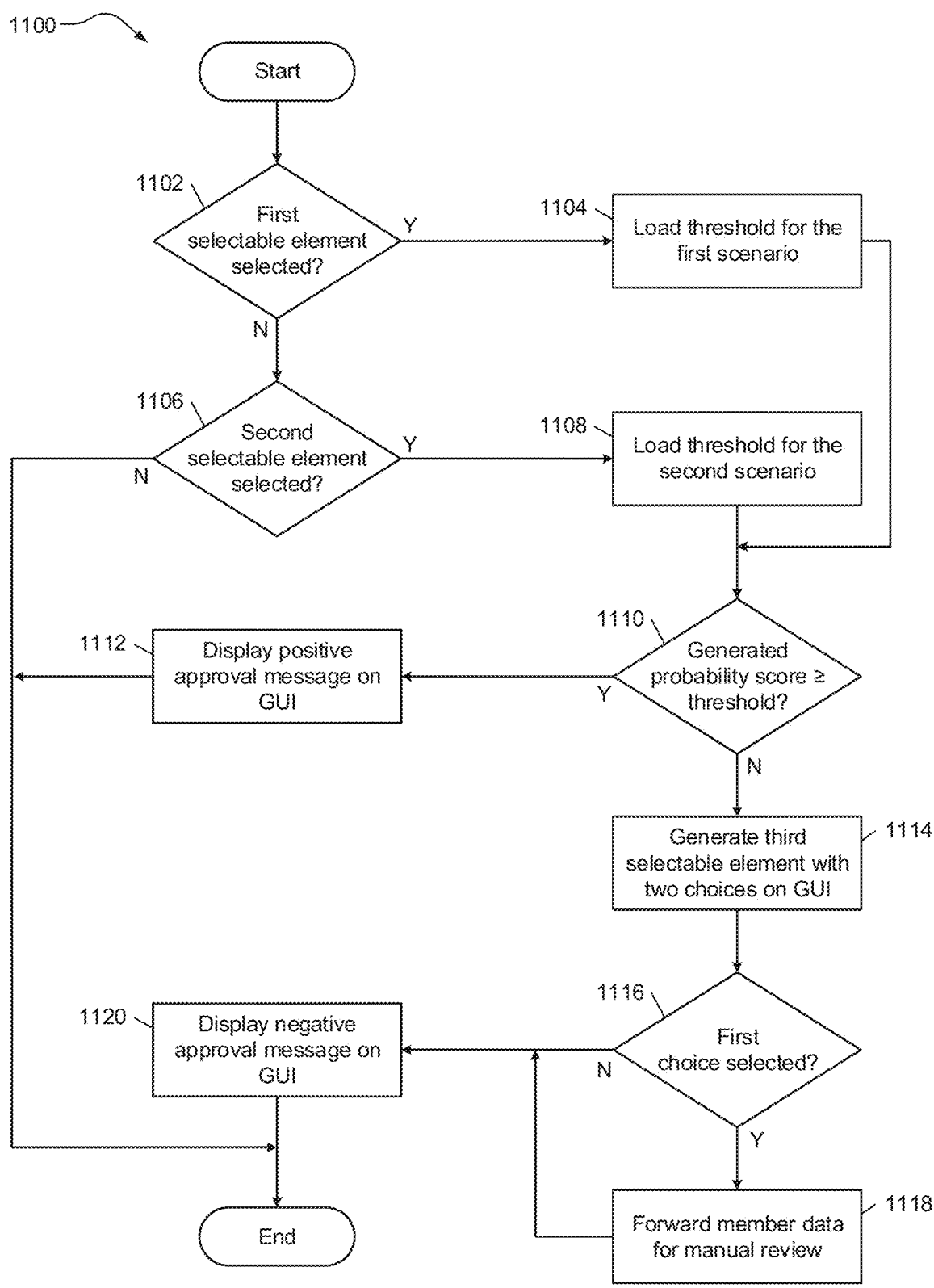
FIG. 11 is a flowchart of an example process for transforming a user interface according to an output of a trained machine learning model.

FIG. 11 is a flowchart of an example process 1100 which may be performed by the machine learning module 132 and/or the user interface transformation module 134 at step 1026 of process 1000 of FIG. 10 to transform the graphical user interface based on the generated probability score p.

Control begins at 1102 by determining whether the first selectable graphical user interface element was selected in process 1000. If at 1102, control determines that the first selectable graphical user interface element was selected, control proceeds to 1104. Otherwise, control proceeds to 1106. At 1106, control determines whether the second selectable element was selected. If at 1106, control determines the second selectable element was selected, control proceeds to 1108. At 1104, control loads a threshold $t_1$ for the first scenario. The threshold $t_1$ may be the threshold probability score output by the trained machine learning model at or above which the system 100 will automatically approve the prior authorization case.

In various implementations, the threshold $t_1$ may be determined by testing historical data against the trained machine learning model. For example, the historical data may include each of the explanatory variables relevant to the selected scenario, as well as whether each prior authorization case was approved upon manual review. In various implementations, the training data structure created at step 506 of process 500 may be used. In various implementations, evaluation metrics may be calculated by testing the trained machine learning model against the training data structure. In various implementations, accuracy, false positives, and false negatives may be calculated for a range of threshold values $t_1$.

Accuracy may be defined as the percentage of cases for which the system 100 applying the trained machine learning model returns the same decision as the manual review decision in the training data structure. False positives may be defined as the percentage of cases in which the system 100 applying the trained machine learning model returns an "approved" decision, but the manual review decision in the training data structure has a "not approved" decision. False negatives may be defined as the percentage of cases in which the system 100 applying the trained machine learning model returns a "not approved" decision, but the manual review decision in the training data structure has an "approved" decision. The threshold value $t_1$ may selected based on the accuracy, false positives, and false negatives metrics calculated by testing outputs from the trained machine learning model at the threshold value $t_1$ using the training data structure. In various implementations, a probability threshold $t_1$ in a range of about 0.85 to about 1.00 may be selected. In various implementations, a probability threshold $t_1$ of about 0.95 may be selected. In various implementations, a probability threshold $t_1$ of about 0.98 may be selected. After the probability threshold $t_1$ for the first scenario is loaded, control proceeds to 1110.

At 1108, control loads the threshold $t_2$ for the second scenario. In various implementations, the threshold $t_2$ may be determined in a manner similar to the threshold $t_1$, except by testing the trained machine model for the second scenario against the training data structure. In various implementations, a probability threshold $t_2$ in a range of about 0.85 to about 1.00 may be selected. In various implementations, a probability threshold $t_2$ of about 0.95 may be selected. In various implementations, a probability threshold $t_2$ of about 0.98 may be selected. After the probability threshold $t_2$ for the second scenario is loaded, control proceeds to 1110.

At 1110, control determines whether the probability score p generated by the loaded machine learning model at step 1022 of process 1000 is greater than or equal to the loaded probability threshold $t_1$ or $t_2$. If at 1110, the answer is yes, control proceeds to 1112. Otherwise, control proceeds to 1114. At 1112, control displays a positive approval message on the graphical user interface. At 1114, control generates a third selectable element on the graphical user interface. In various implementations, the third selectable element may include two selectable choices. For example, a first selectable choice of the third selectable element may include a textual and/or graphical message prompting the user to forward the denied prior authorization case to a physician, pharmacist, and/or other qualified professional for manual review, while a second selectable choice of the third selectable element may include a textual and/or graphical message prompting the user not to forward the case. Control proceeds to 1116.

At 1116, control determines whether the first selectable choice of the third selectable element was selected. If at 1116, control determines that the first selectable choice was selected, control proceeds to 1118. Otherwise, control proceeds to 1120. At 1118, control automatically forwards a data package which includes the prior authorization case (including any relevant member data) to the physician, pharmacist, and/or other qualified professional for manual review. For example, control may forward the data package to a remote computer or mobile device via network 104. Control proceeds to 1120. At 1120, control displays a negative approval message on the graphical user interface.

Figure 12:
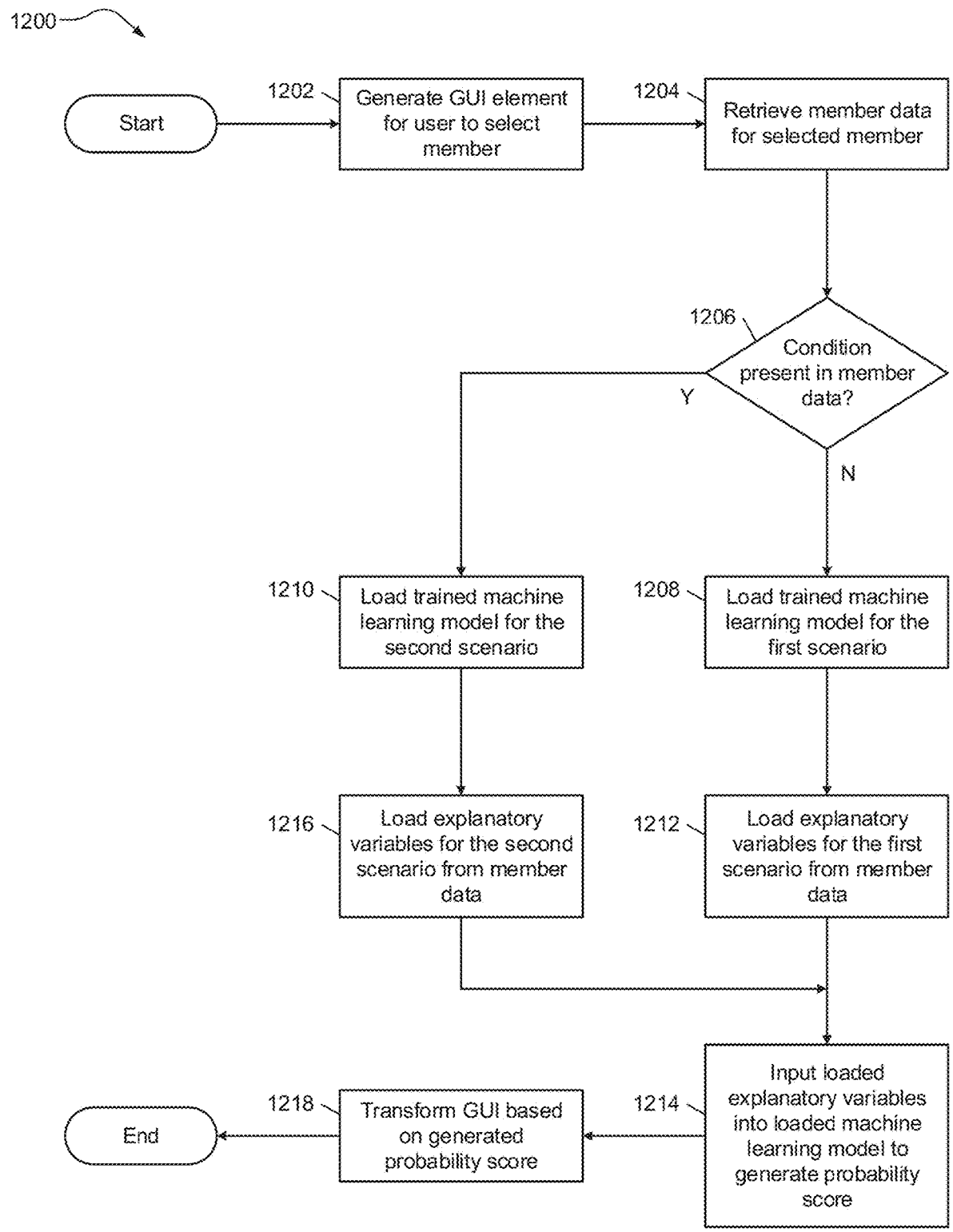
FIG. 12 is a flowchart of an example process for transforming a user interface according to an output of a trained machine learning model.

FIG. 12 is a flowchart of an example process 1200 which may be performed by the machine learning module 132 and/or the user interface transformation module 134 of FIGS. 1 and 4 to generate and transform the user interface according to the trained machine learning model at step 510 of process 500 of FIG. 5. Control begins at 1202 by generating a graphical user interface element for the user to select a member. In various implementations, the graphical user interface element may be a textual search box allowing the user to search for members present in member data 120. In various implementations, the graphical user interface element may be a drop-down menu allowing the user to select a member present in member data 120. After the user selects a member, control proceeds to 1204. At 1204, control retrieves member data for the selected member and proceeds to 1206.

At 1206, control determines whether a condition is present in the member data. In various implementations, the condition at 1206 may be the same condition as the condition of step 712 of process 700. In various implementations, the condition may be whether a positive diagnosis for rheumatoid arthritis is present in the medical records of the selected member. If at 1206, control determines that the condition is not true, control proceeds to 1208. If at 1206, control determines that the condition is true, control proceeds to 1210. At 1208, control loads the trained machine learning model for the first scenario. For example, control may load the trained machine learning model described by Equation (3). Control proceeds to 1212. At 1212, control loads the relevant explanatory variables $x_i$ through $x_j$ for the loaded trained machine learning model from the member data 120 for the selected member, and provides the explanatory variables to the trained machine learning model. For example, the explanatory variables may be those defined by Table 1 above. Control proceeds to 1214.

At 1210, control loads the trained machine learning model for the second scenario. For example, control may load the trained machine learning model described by Equation (4). Control proceeds to 1216. At 1216, control loads the relevant explanatory variables $x_i$ through $x_j$ for the loaded trained machine learning model from the member data 120 for the selected member, and provides the explanatory variables to the trained machine learning model. For example, the explanatory variables may be those defined by Table 2 above. Control proceeds to 1214.

At 1214, control inputs the loaded explanatory variables into the loaded machine learning model to generate a probability score p. Control proceeds to 1218 and transforms the graphical user interface based on the generated probability score p.

Figure 13:
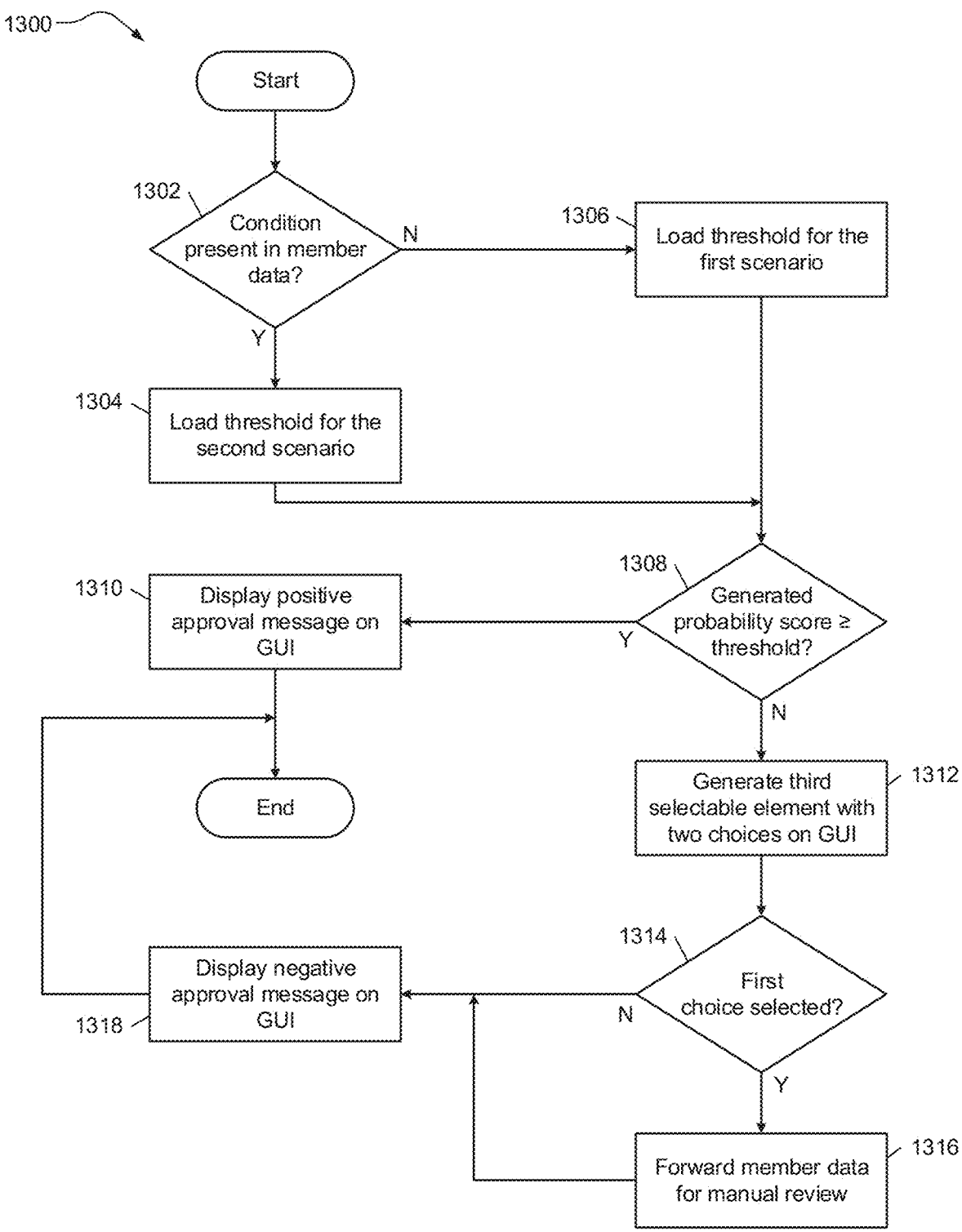
FIG. 13 is a flowchart of an example process for transforming a user interface according to an output of a trained machine learning model.

FIG. 13 is a flowchart of an example process 1300 which may be performed by the machine learning module 132 and/or the user interface transformation module 134 at step 1218 of process 1200 of FIG. 12 to transform the graphical user interface based on the generated probability score p. Control begins at 1302 by determining whether the condition was present in the member data 120 at step 1206 of process 1200. If at 1302, control determines that the condition was present, control proceeds to 1304. Otherwise, control proceeds to 1306. At 1304, control loads the probability threshold $t_2$ for the second scenario. The probability threshold $t_2$ may be determined the same way as the probability threshold $t_2$ of step 1108 of process 1100. In various implementations, a probability threshold $t_2$ in a range of about 0.85 to about 1.00 may be selected. In various implementations, a probability threshold $t_2$ of about 0.95 may be selected. In various implementations, a probability threshold $t_2$ of about 0.98 may be selected. After the probability threshold $t_2$ is loaded, control proceeds to 1308.

At 1306, control loads the probability threshold $t_1$ for the first scenario. The probability threshold $t_1$ may be determined the same way as the probability threshold $t_1$ of step 1104 of process 1100. In various implementations, a probability threshold $t_1$ in a range of about 0.85 to about 1.00 may be selected. In various implementations, a probability threshold $t_1$ of about 0.95 may be selected. In various implementations, a probability threshold $t_1$ of about 0.98 may be selected. After the probability threshold $t_1$ is loaded, control proceeds to 1308.

At 1308, control determines whether the probability score p generated by the loaded machine learning model at step 1022 of process 1000 is greater than or equal to the loaded probability threshold $t_1$ or $t_2$. If at 1308, the answer is yes, control proceeds to 1310. Otherwise, control proceeds to 1312. At 1310, control displays a positive approval message on the graphical user interface. At 1312, control generates a third selectable element on the graphical user interface. In various implementations, the third selectable element may include two selectable choices. For example, a first selectable choice of the third selectable element may include a textual and/or graphical message prompting the user to forward the denied prior authorization case to a physician, pharmacist, and/or other qualified professional for manual review, while a second selectable choice of the third selectable element may include a textual and/or graphical message prompting the user not to forward the case. Control proceeds to 1314.

At 1314, control determines whether the first selectable choice of the third selectable element was selected. If at 1314, control determines that the first selectable choice was selected, control proceeds to 1316. Otherwise, control proceeds to 1318. At 1316, control automatically forwards a data package which includes the prior authorization case (including any relevant member data) to the physician, pharmacist, and/or other qualified professional for manual review. For example, control may forward the data package to a remote computer or mobile device via network 104. At 1318, control displays a negative approval message on the graphical user interface.

Conclusion

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in a different order (or concurrently) without altering the principles of the present disclosure. Unless indicated otherwise, numbering or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements.

The phrase "at least one of A, B, and C" should be construed to mean a logical (A OR B OR C), using a non-exclusive logical OR, and should not be construed to mean "at least one of A, at least one of B, and at least one of C." The term "set" does not necessarily exclude the empty set—in other words, in some circumstances a "set" may have zero elements. The term "non-empty set" may be used to indicate exclusion of the empty set—in other words, a non-empty set will always have one or more elements. The term "subset" does not necessarily require a proper subset. In other words, a "subset" of a first set may be coextensive with (equal to) the first set. Further, the term "subset" does not necessarily exclude the empty set—in some circumstances a "subset" may have zero elements.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2020 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. Such apparatuses and methods may be described as computerized apparatuses and computerized methods. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The invention claimed is:

1. A computerized method for transforming an interactive graphical user interface according to machine learning, the method comprising:
   selecting a persona from a data store, wherein the data store is stored by a remote networked storage device that is remote from the interactive graphical user interface;
   loading, into a data processing module, a data structure from the remote networked storage device, wherein the data structure is associated with the selected persona;
   generating the interactive graphical user interface comprising:
      a first selectable element, and
      a second selectable element;
   in response to a user selecting the first selectable element:
      loading, at the data processing module, a first trained machine learning model from the remote networked storage device,
      loading, at the data processing module, a first set of explanatory variables from the data structure, inputting, at the data processing module, the first set of explanatory variables to the first trained machine learning model to generate a first metric, and transforming the user interface according to the selected persona and the first metric;

in response to the user selecting the second selectable element:

loading, at the data processing module, a second trained machine learning model from the remote networked storage device, loading, at the data processing module, a second set of explanatory variables from the data structure, inputting, at the data processing module, the second set of explanatory variables to the second trained machine learning model to generate a second metric, and transforming the user interface according to the selected persona and the second metric, wherein the first trained machine learning model is different from the second trained machine learning model, and wherein the first metric is a first probability of a user described by the persona being approved for a first prior authorization prescription; and automatically approving the first prior authorization prescription in response to reaching a first threshold value.

2. The method of claim 1, wherein the second metric is a second probability of the user described by the persona being approved for a second prior authorization prescription.

3. The method of claim 1, wherein transforming the user interface according to the selected persona and the first metric comprises:

loading, at the data processing module, the first threshold value;

determining whether the first metric is less than the first threshold value;

in response to determining the first metric is less than the first threshold value, generating an interactive user interface element having a first selectable option and a second selectable option; and in response to the user selecting the first selectable option:

sending the data structure associated with the selected persona to a remote user, and transforming the user interface to display a negative approval message.

4. The method of claim 3, further comprising:

in response to the user selecting the second selectable option, transforming the user interface to display the negative approval message.

5. The method of claim 4, further comprising:

in response to determining that the first metric is not less than the first threshold value, transforming the user interface to display a positive approval message.

6. The method of claim 1, wherein transforming the user interface according to the selected persona and the second metric comprises:

loading, at the data processing module, a second threshold value;

determining whether the second metric is less than the second threshold value;

in response to determining the second metric is less than the second threshold value, generating an interactive user interface element having a first selectable option and a second selectable option; and in response to the user selecting the first selectable option:

sending the data structure associated with the selected persona to a remote user, and transforming the user interface to display a negative approval message.

7. The method of claim 6, further comprising:

in response to the user selecting the second selectable option, transforming the user interface to display the negative approval message.

8. The method of claim 7, further comprising:

in response to determining the second metric is not less than the second threshold value, transforming the user interface to display a positive approval message.

9. A computerized method for transforming a user interface according to machine learning, the method comprising:

selecting a persona from a data store, wherein the data store is located at a remote networked storage device;

loading, into a data processing module, a data structure from the remote networked storage device, wherein the data structure associated with the selected persona;

determining, at the data processing module, whether a condition is present in the data structure;

in response to determining the condition is not present in the data structure:

loading, at the data processing module, a first trained machine learning model from the remote networked storage device, loading, at the data processing module, a first set of explanatory variables from the data structure, inputting, at the data processing module, the first set of explanatory variables to the first trained machine learning model to generate a first metric, and transforming the user interface according to the selected persona and the first metric;

in response to determining the condition is present in the data structure:

loading, at the data processing module, a second trained machine learning model from the remote networked storage device, loading, at the data processing module, a second set of explanatory variables from the data structure, inputting, at the data processing module, the second set of explanatory variables to the second trained machine learning model to generate a second metric, and transforming the user interface according to the selected persona and the second metric, wherein the first trained machine learning model is different from the second trained machine learning model, and wherein the first metric is a first probability of a user described by the persona being approved for a first prior authorization prescription; and automatically approving the first prior authorization prescription in response to reaching a first threshold value.

10. The method of claim 9, wherein the condition is a presence of a diagnosis for rheumatoid arthritis.

11. The method of claim 9, wherein the second metric is a second probability of the user described by the persona being approved for a second prior authorization prescription.

12. The method of claim 9, wherein transforming the user interface according to the selected persona and the first metric comprises:

loading, at the data processing module, the first threshold value;

determining whether the first metric is less than the first threshold value;

in response to determining the first metric is less than the first threshold value, generating an interactive user interface element having a first selectable option and a second selectable option; and in response to the user selecting the first selectable option:
sending the data structure associated with the selected persona to a remote user, and
transforming the user interface to display a negative approval message.

13. The method of claim 12, further comprising:
in response to the user selecting the second selectable option, transforming the user interface to display the negative approval message.

14. The method of claim 13, further comprising:
in response to determining that the first metric is not less than the first threshold value, transforming the user interface to display a positive approval message.

15. The method of claim 9, wherein transforming the user interface according to the selected persona and the second metric comprises:
loading, at the data processing module, a second threshold value;
determining whether the second metric is less than the second threshold value;
in response to determining the second metric is less than the second threshold value, generating an interactive user interface element having a first selectable option and a second selectable option; and
in response to the user selecting the first selectable option:
sending the data structure associated with the selected persona to a remote user, and
transforming the user interface to display a negative approval message.

16. The method of claim 15, further comprising:
in response to the user selecting the second selectable option, transforming the user interface to display the negative approval message.

17. The method of claim 16, further comprising:
in response to determining that the second metric is not less than the second threshold value, transforming the user interface to display a positive approval message.

18. A system for transforming a user interface according to machine learning, comprising:
a first data store comprising a persona and a data structure associated with the persona;
a second data store on a remote networked storage device, wherein the second data store comprises:
at least one of a first trained machine learning model and a second trained machine learning model, and
at least one of a first set of explanatory variables and a second set of explanatory variables; and
a processor operatively coupled to the first data store and the second data store via a network; a network, wherein the processor is configured by a set of instructions to:
p1 generate a graphical user interface comprising a first selectable element and a second selectable element,
in response to a user selecting the first selectable element:
input the first set of explanatory variables to the first trained machine learning model to generate a first metric, and
transform the user interface according to the persona and the first metric, in response to the user selecting the second selectable element:
input the second set of explanatory variables to the second trained machine learning model to generate a second metric, and
transform the user interface according to the persona and the second metric,
wherein the first trained machine learning model is different from the second trained machine learning model, and
wherein the first metric is a first probability of a user associated with the persona being approved for a first prior authorization prescription, and
automatically approve the first prior authorization prescription in response to reaching a threshold value.

19. The system of claim 18, wherein the second metric is a second probability of the user associated with the persona being approved for a second prior authorization prescription.

20. The system of claim 18, wherein:
the second data store comprises the threshold value; and
the processor is further configured by the set of instructions to:
determine whether the first metric is less than the threshold value,
in response to determining that the first metric is less than the threshold value, generate an interactive user interface element having a first selectable option and a second selectable option, and
in response to the user selecting the first selectable option:
send the data structure associated with the persona to a remote user, and transform the user interface to display a negative approval message.

* * * * *